United States Patent
Kiedrowski et al.

(10) Patent No.: US 10,481,383 B2
(45) Date of Patent: Nov. 19, 2019

(54) ENDOSCOPIC OPTICAL SYSTEM

(71) Applicant: OLYMPUS WINTER & IBE GMBH, Hamburg (DE)

(72) Inventors: Gregor Kiedrowski, Hamburg (DE); Peter Schouwink, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 15/541,735

(22) PCT Filed: Dec. 16, 2015

(86) PCT No.: PCT/EP2015/002531
§ 371 (c)(1),
(2) Date: Jul. 6, 2017

(87) PCT Pub. No.: WO2016/110303
PCT Pub. Date: Jul. 14, 2016

(65) Prior Publication Data
US 2018/0024347 A1  Jan. 25, 2018

(30) Foreign Application Priority Data
Jan. 9, 2015  (DE) .......... 10 2015 000 050

(51) Int. Cl.
*G02B 6/00* (2006.01)
*G02B 23/24* (2006.01)
(Continued)

(52) U.S. Cl.
CPC ........ *G02B 23/2407* (2013.01); *A61B 1/0011* (2013.01); *A61B 1/0017* (2013.01);
(Continued)

(58) Field of Classification Search
USPC .......................................................... 385/11
See application file for complete search history.

(56) References Cited

U.S. PATENT DOCUMENTS

| 4,153,333 A * | 5/1979 | Harada ............ | G02B 6/06 385/116 |
| 4,760,839 A * | 8/1988 | Nagasaki ........... | G02B 6/06 359/489.15 |

(Continued)

FOREIGN PATENT DOCUMENTS

| DE | 3435114 A1 | 5/1985 |
| DE | 69923388 T2 | 12/2005 |

(Continued)

OTHER PUBLICATIONS

English translation of International Preliminary Report on Patentability dated Jul. 20, 2017 together with the Written Opinion received in related International Application No. PCT/EP2015/002531.

(Continued)

*Primary Examiner* — Kaveh C Kianni
(74) *Attorney, Agent, or Firm* — Scully, Scott, Murphy & Presser, P.C.

(57) ABSTRACT

An endoscopic optical system including: a fiber image conductor arranged in an elongated shaft tube, the fiber image conductor having a proximal face; an objective arranged distally relative to the fiber image conductor; an observation device arranged proximally relative to the proximal face of the fiber image conductor; a mask; and a transparent cover pane arranged between the proximal face of the fiber image conductor and the observation device; wherein the transparent cover pane is configured as a moire filter.

4 Claims, 2 Drawing Sheets

(51) Int. Cl.
*G02B 5/30* (2006.01)
*G02B 23/26* (2006.01)
*G02B 27/10* (2006.01)
*A61B 1/00* (2006.01)
*G02B 27/00* (2006.01)

(52) U.S. Cl.
CPC ........ *A61B 1/00186* (2013.01); *G02B 5/3083* (2013.01); *G02B 23/243* (2013.01); *G02B 23/2476* (2013.01); *G02B 23/26* (2013.01); *G02B 27/0025* (2013.01); *G02B 27/1066* (2013.01)

(56) References Cited

U.S. PATENT DOCUMENTS

| | | | | |
|---|---|---|---|---|
| 4,805,028 | A * | 2/1989 | Nishioka | G02B 23/2484 348/342 |
| 4,867,136 | A * | 9/1989 | Suzuki | A61B 1/0008 600/109 |
| 4,870,559 | A * | 9/1989 | Hyatt | B60R 16/0373 318/640 |
| 5,392,067 | A * | 2/1995 | Konno | H04N 5/357 348/65 |
| 5,427,103 | A * | 6/1995 | Fujio | A61B 1/0051 600/101 |
| 5,521,726 | A * | 5/1996 | Zimmerman | G02B 5/3025 349/159 |
| 6,025,873 | A * | 2/2000 | Nishioka | A61B 1/00195 348/342 |
| 6,141,034 | A * | 10/2000 | McCutchen | G02B 27/22 348/36 |
| 6,356,700 | B1 * | 3/2002 | Strobl | G02B 6/0006 359/859 |
| 6,992,718 | B1 * | 1/2006 | Takahara | G02B 23/14 348/333.09 |
| 2002/0128539 | A1 * | 9/2002 | Higuma | A61B 1/00188 600/133 |
| 2002/0159728 | A1 | 10/2002 | Kobayashi et al. | |
| 2007/0115477 | A1 * | 5/2007 | Teramura | G01J 3/4535 356/479 |
| 2010/0194974 | A1 * | 8/2010 | Hoshikawa | G03B 17/14 348/373 |
| 2012/0140883 | A1 * | 6/2012 | Iwakiri | A61B 6/4233 378/62 |

FOREIGN PATENT DOCUMENTS

| | | | |
|---|---|---|---|
| JP | S59-71022 A | 4/1984 | |
| JP | 59129820 A * | 7/1984 | ........ G02B 23/2484 |
| JP | S59-129820 A | 7/1984 | |
| JP | S60-076712 A | 5/1985 | |
| JP | H07-325258 A | 12/1995 | |
| JP | 2002328311 A * | 11/2002 | ............. G02B 6/065 |

OTHER PUBLICATIONS

International Search Report dated Mar. 9, 2016 issued in PCT/EP2015/002531.

* cited by examiner

ENDOSCOPIC OPTICAL SYSTEM

CROSS-REFERENCE TO RELATED APPLICATION

The present application is based upon and claims the benefit of priority from PCT/EP2015/002531 filed on Dec. 16, 2015, which claims benefit to DE 10 201 500 0050.0 filed on Jan. 9, 2015, the entire contents of each of which are incorporated herein by reference.

BACKGROUND

Field

The present invention generally relates to endoscopes, and more specifically to endoscopic optical systems.

Prior Art

Endoscopic optical systems with a fiber image conductor produce an image with a rasterization caused by the fiber image conductor. Additional rasters can be layered, e.g. by means of rasterizations occurring in the image, such as occurring when observing a finely rasterized surface. Finally, it is important to take into account the rasterization of a digital camera with which the image of the endoscopic optical system is recorded in the operational manner that is common nowadays.

However, if a plurality of grids is superimposed, it can result in moire effects that lead to serious impairments in the evaluation of the images. This cannot be allowed, particularly in the case of medical optics.

Therefore, in endoscopic optical systems, moire filters are common, which produce a defined slight blurring. So, the moire also then disappears.

Moire filters are commonly used in the form of plates consisting of crystalline material with birefringent properties. Frequently, the moire filters are located in the cameras in which they are already provided, for example, in high-quality consumer cameras.

A fiber image conductor is susceptible to dirt on its proximal face and requires a protective covering there, for example, in the form of a glass pane. There is also a mask there, for example, in the form of a circumferential ring around the edge, which covers a region of the image. Masks are to be provided in the region of the proximal face of the fiber image conductor, since the common endoscopic optical system produces a sharp intermediate image there.

The structural conditions in this region are complicated and lead to high manufacturing costs. Efforts have also been made to save the moire filter in the camera.

SUMMARY

An object is to solve the aforementioned structural problems in the region of the proximal face of the fiber image conductor in an endoscopic optical system of the type discussed above.

Accordingly, the covering disk can be configured as a moire filter. Thus, one of the two components previously provided, namely the moire filter and the covering pane, has been saved. Problems do not arise, since the common moire filters are designed as plates, which can also be used for covering purposes.

The moire filter can be divided into a plurality of birefringent layers which are arranged so that they produce blurring in different directions. Thus, raster effects in different directions can be controlled.

Alternatively, three birefringent layers can be provided. A good moire control can be achieved even in the case of rasterizations formed at unfavourable oblique angles.

Masks can be attached in the immediate region of the proximal face of the fiber image conductor due to achieve sharper imaging. They can be used for different purposes, for example as an annular representation of an edge limitation or even as a crosshair or the like. The moire filter can form a pane covering the proximal face of the fiber image conductor, which with its distal face can be located in the vicinity of the proximal face of the fiber image conductor. This surface is therefore suitable for attaching the mask, which can lead to a very simple manufacturing construction, in which, namely, the two parts that are difficult with respect to the alignment precision, namely the mask and the moire filter, can be precisely prefabricated as a component.

The mask can be cut from a thin sheet, which enables precise edge structures. However, the sheet must then be fixed, for example, to the distal face of the moire filter. In this way, the manufacture can be simplified, in that the mask is vaporized on the distal face of the moire filter. Precise manufacturing and, in particular, precise alignments are easily achievable.

In known constructions, the covering panes are arranged at a distance from the proximal face of the fiber image conductor. This separate arrangement can lead to disruptive alignment errors. Accordingly, the moire filter can be adhered with its distal face to the proximal face of the fiber image conductor. This provides for a very precise fixing of these two parts together, with which adjustment errors can be avoided from the outset. In addition, the penetration of impurities, such as dust into the sharp imaging region on the proximal face of the fiber image conductor, is avoided.

DETAILED DESCRIPTION

Figure 1:
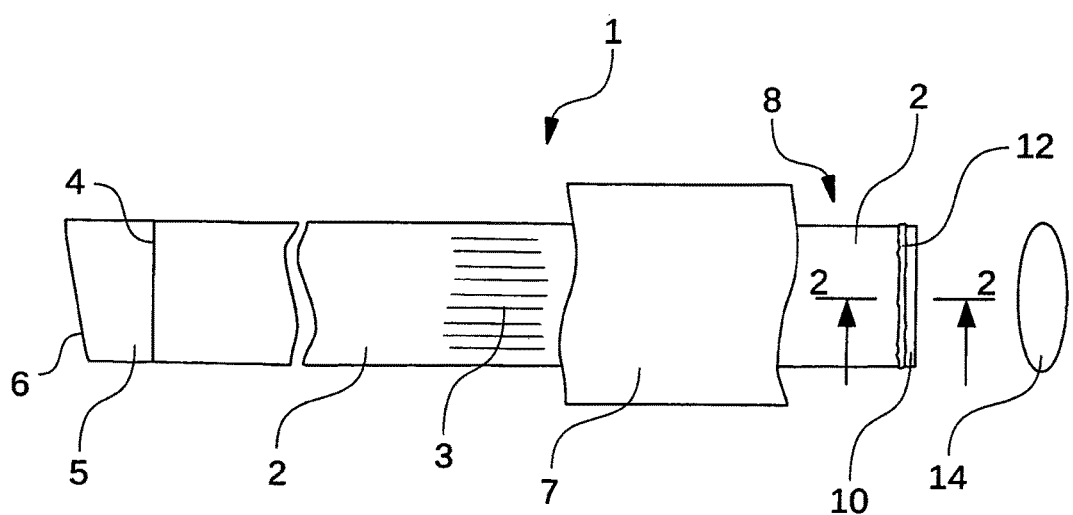
FIG. 1 illustrates a partial sectional side view of an endoscopic optical system.

FIG. 1 shows an endoscopic optical system, which substantially consists of a fiber image conductor 2, the individual fibers 3 of which are indicated in FIG. 1.

The fiber image conductor 2 is connected at a distal face 4 to an objective 5, which, for example, has an oblique face 6, as illustrated.

The illustrated endoscopic optical system 1 is commonly arranged in a very elongated shape and, for extra protection, in a shaft tube 7, which can be designed rigid or even flexible.

Figure 2:
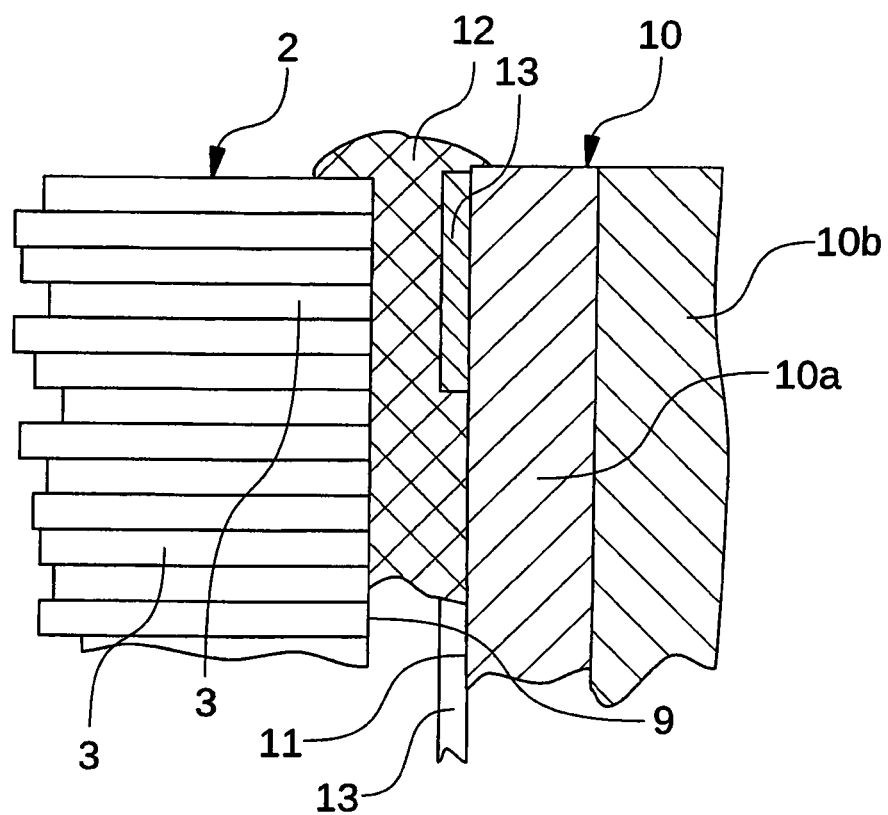
FIG. 2 illustrates a greatly enlarged section as taken along line 2-2 in FIG. 1.

The proximal end region 8 of the fiber image conductor 2 is illustrated in a significantly enlarged sectional view in FIG. 2.

The fiber image conductor 2, consisting of different fibers 3 in a parallel arrangement, can be seen. The fibers illustrated all end at their distal end in a proximal face 9. Towards the proximal face, the ends of the fibers 3 illustrated in FIG. 2 are illustrated broken off.

As shown in FIG. 2, arranged at a distance from the proximal face 9 of the fiber image conductor 2 is a moire filter 10, which is configured as a flat-parallel plate and with its distal face 11 at a small distance from the proximal face 9 of the fiber image conductor 2.

The moire filter 10 consists of a plurality of layers, e.g. three layers, of which two layers 10*a* and 10*b* are illustrated in FIG. 2. These consist, for example, of birefringent quartz and produce a birefringent effect at different angles, which, for example, are below 60° to one another. With three layers, a good moire control can be ensured even with difficult rasterization.

As FIG. 2 shows, the distal face 11 of the moire filter 10 and the proximal face 9 of the fiber image conductor 2 are at a small distance from one another, which is filled with adhesive 12, as shown in FIG. 2. This can, as illustrated in both figures, protrude somewhat at the edge in order to ensure a careful sealing. The adhesive provides a very strong and stable connection.

Arranged at the distal face 11 of the moire filter 10 is a mask 13, which in the exemplary embodiment is configured as a vaporized metal film, the thickness of which has been greatly exaggerated in FIG. 2 for better illustration.

As is also shown in FIG. 2, the mask 13 is attached before adhesion, so that it is completely enclosed by the adhesive 12.

FIG. 1 shows an eyepiece lens 14 which is arranged proximally at a distance in front of the proximal end of the fiber image conductor 2. With it, the sharp image appearing at the proximal face 9 of the fiber image conductor 2 can be observed, for example with the naked eye or with a camera.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

1 Endoscopic optical system
2 Fiber image conductor
3 Fibers
4 Distal face of 2
5 Objective
6 Oblique face
7 Shaft tube
8 Proximal end region
9 Proximal face
10 Moire filter
10*a* Layer
10*b* Layer
11 Distal face of 10
12 Adhesive
13 Mask
14 Eyepiece lens

The invention claimed is:

1. An endoscopic optical system comprising:
a fiber image conductor arranged in an elongated shaft tube, the fiber image conductor having a proximal face;
an objective arranged distally relative to the fiber image conductor;
an observation device arranged proximally relative to the proximal face of the fiber image conductor;
a mask formed of metal; and
a transparent cover pane arranged between the proximal face of the fiber image conductor and the observation device;
wherein the transparent cover pane is configured as a moire filter; and
the mask is a metal vapor deposition layer on a distal face of the moire filter and attached to the image conductor via an adhesive.

2. The endoscopic optical system according to claim 1, wherein the moire filter comprises a plurality of birefringent layers, each of the plurality of birefringent layers being arranged parallel to the distal face of the moire filter, the plurality of birefringent layers being arranged so as to produce blurring in different directions parallel to the distal face.

3. The endoscopic optical system according to claim 2, wherein the plurality of birefringent layers comprises three birefringent layers.

4. The endoscopic optical system according to claim 1, further comprising an adhesive disposed on the distal face of the moire filter to adhere the proximal face of the fiber image conductor to the distal face of the moire filter.

* * * * *